United States Patent [19]

Bennett et al.

[11] 4,147,628
[45] Apr. 3, 1979

[54] BLOOD PARTITIONING METHOD

[75] Inventors: Michael C. Bennett, Summit, N.J.; Suresh N. Mehta, Bombay, India

[73] Assignee: Becton, Dickinson and Company, Rutherford, N.J.

[21] Appl. No.: 871,551

[22] Filed: Jan. 23, 1978

[51] Int. Cl.$^2$ ............................................. B01D 21/00
[52] U.S. Cl. ..................................... 210/83; 210/516; 210/518; 210/DIG. 23; 210/DIG. 24
[58] Field of Search ................... 210/83, 84, 513, 516, 210/518, DIG. 24, DIG. 23, 361; 233/1 A, 1 R, 26; 23/258.5, 259, 292; 106/287 SB; 128/2 R, 2 F, 2 G, 214 R, 214 Z, 272, 276

[56] References Cited

U.S. PATENT DOCUMENTS

| | | | |
|---|---|---|---|
| 3,750,645 | 8/1973 | Bennett et al. | 210/DIG. 23 |
| 3,852,194 | 12/1974 | Zine | 210/DIG. 23 |
| 3,901,219 | 8/1975 | Kay | 210/DIG. 23 |

Primary Examiner—Frank Sever
Attorney, Agent, or Firm—Kane, Dalsimer, Kane, Sullivan and Kurucz

[57] ABSTRACT

The disclosure is of an improved method and apparatus for separating blood into light, substantially liquid phase and its heavy, substantially cellular phase by centrifuging a blood filled container having disposed therein an inert, gel-like barrier material possessing a density intermediate between the two phases of the blood. The improvement comprises employing a constricted tubular container, the constriction being at the zone where it is calculated the gel-like barrier material will align during centrifugation.

3 Claims, 4 Drawing Figures

BLOOD PARTITIONING METHOD

BACKGROUND OF THE INVENTION

1. Field of the Invention

The invention related to methods and apparatus for the collection and separation of the light liquid phase from the heavy, substantially celluar phase of blood.

2. Brief Description of the Prior Art

The U.S. Pat. Nos. 3,852,194; 3,920,549; and 3,997,442 are representative of the prior art. In general, the prior art apparatus comprises a tubular container into which there is inserted a gel-like barrier material having a density intermediate between that found for the light, liquid phase and the heavy, substantially cellular phases of blood. Generally, the gel-like material is disposed at the bottom end of the tube and then the tubular collection container is filled with blood. Upon centrifugation, the blood is gradient separated into its two phases and the gel-like barrier material migrates to the interface between phases. Upon completion of centrifugation, the gel-like barrier material forms a physical and chemical barrier between the separated blood phases.

On occasion, there is difficulty with the prior art methods and apparatus in establishing a complete barrier with the gel-like material between the separated blood phases. This is particularly so when the tube is centrifuged in a fixed angle head centrifuge. In such instances there is a tendency for the gel-like barrier material to migrate to its final position along one portion of the inner wall of the tubular container. When the gel-like material reaches the zone for its density gradient, it may not migrate completely to the opposite wall of the tubular container to affect a complete barrier between the separated blood phases. If the gel-like material does reach the opposing tubular wall, it may not adhere sufficiently so that in subsequent handling it will peel back and off the opposing wall. This of course is undesirable under many circumstances.

By the method of our invention, the above described difficulty of the prior art is obviated. A strong bond is obtained between the gel-like barrier material and the entire surrounding walls of the tubular container. This is particularly advantageous if the collected blood specimen is to be stored for a long period of time, or is likely to be subjected to temperature shocks during storage or shocks due to transportation.

SUMMARY OF THE INVENTION

The invention comprises, in the method of separating blood into its light, substantially liquid phase and its heavy, substantially celluar phase by providing a tubular blood collection container having disposed at its bottom an inert, flowable, gel-like barrier material; filling the container with blood; and centrifuging the blood filled container to affect separation of phases and displacement of the barrier material to the interface between phases; the improvement which comprises, providing as the tubular container, one having a constriction in the bore thereof, positioned in the zone where the barrier material will come to rest during centrifugation, said constriction being integrally formed and fixed in the wall of said container.

DETAILED DESCRIPTION OF THE PREFERRED EMBODIMENTS OF THE INVENTION

A complete understanding of the method of the invention may be obtained from the following description when read in conjunction with the accompanying drawings of FIGS. 1 through 4, inclusive.

Figure 1:
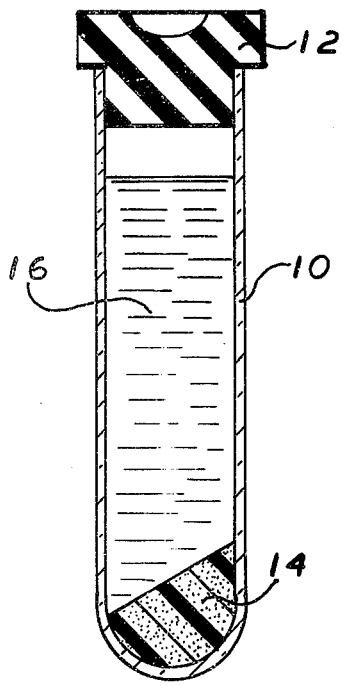
FIG. 1 is a cross sectional side elevation of a prior art tubular blood collection container employed to separate blood into its component phases.
Figure 2:
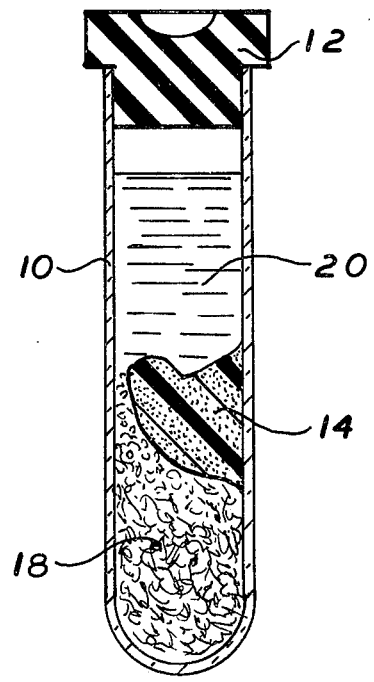
FIG. 2 is a view of the tubular collection container seen in FIG. 1 but after separation of the blood into its component phases.

FIG. 1 is a cross sectional side elevation of a typical tubular blood collection assembly employed in the prior art. The tube 10 is closed with a stopper 12 and has a gel-like barrier material 14 disposed at its lower end. The gel-like material 14 generally has a density intermediate between that of the light, liquid phase of blood and that of the heavy, substantially cellular phase of blood following separation of the blood by centrifugation. The method of separation comprises filling the tubular container 10 with blood 16 and centrifuging it to effect separation of the blood into its component phases. During centrifugation, the gel-like barrier material 14 migrates to the interface between the blood phases to form a physical and chemical barrier between the separate phases. Periodically, particularly when the tube is centrifuged in a fixed angle lead centrifuge the barrier will adhere to only a portion of the container wall during its migration to the interface between separate components of the blood. As shown in FIG. 2, a cross-sectional side elevation of the tubular blood collection container shown in FIG. 1 but following centrifugation of the container blood 16, one can see the result. As shown in FIG. 2, the blood following centrifugation has been separated into its substantially cellular portion 18 and its light liquid phase or serum 20. The gel-like barrier material 14 has formed only a partial barrier between the separated phases 18, 20. Even if the barrier material 14 does effect contact with the opposing wall of tube 10, adhesion may be so light that the barrier "peels off" following handling or transportation of the tubular container 10 or due to tendency of the clot to stretch and expand subsequent to centrifugation.

Figure 3:
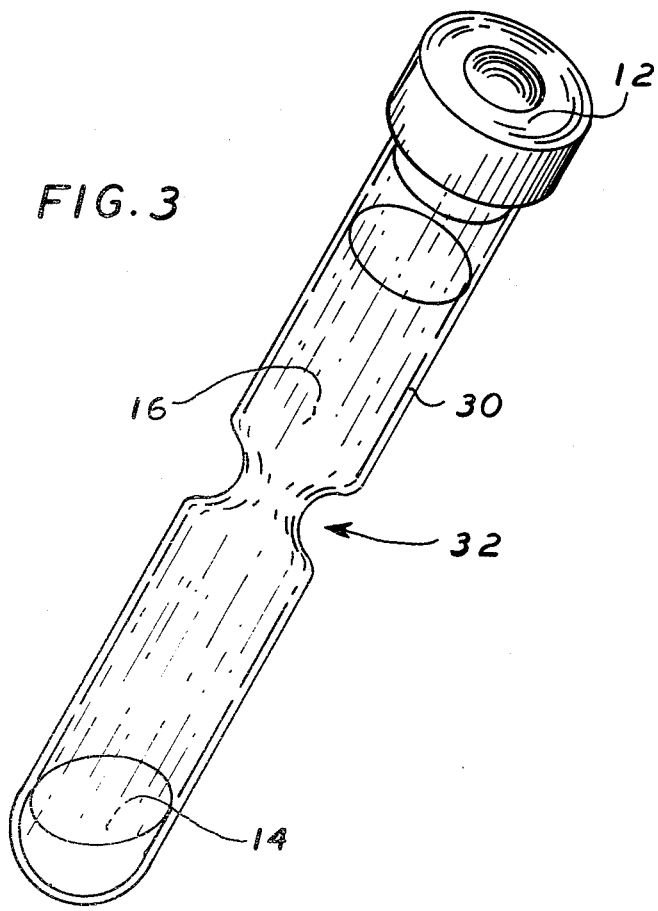
FIG. 3 is an isometric view of the tubular blood collection container employed in the method of the present invention.
Figure 4:
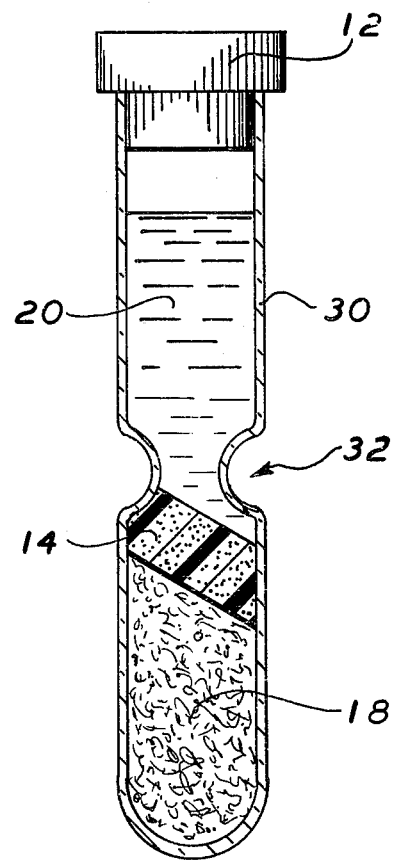
FIG. 4 is a cross sectional side elevation of the tubular container seen in FIG. 3 but after separation of contained blood into its component phases.

The improved method of the present invention corrects the faulty formation of a barrier between the separated blood phases as described above. The improvement comprises of providing as the blood collection tubular container one having a fixed, integrally formed constriction in the tube wall. Referring now to FIG. 3, an isometric view of a tubular container 30, one may see the improvement. Tube 30 is shown in FIG. 3 as containing the gel-like barrier material 14 disposed at its lower end and blood 16 above it. An annular constriction 32 is integrally formed in the wall of tube 30 at the side where it has been calculated the barrier material 14 will migrate to under centrifugal force. When the blood filled tube 30 is centrifuged, the blood 16 is separated into its components of serum 20 and cellular component 18 as previously described. However, the annular constriction creates a geometrical barrier against the tendency of the gel-like barrier material 14 to lift-up or "peel-off". This constriction also tends to break up the smooth channelized stream of the gel-like material giving rise to convolutions that tend to cause it to adhere strongly even to the portion of the tube wall opposite to the flow channel formed during its travel to its density gradient level. Even if subjected to rough handling, the aforementioned peel back phenomenon does not occur and a fixed barrier is established between the separated blood phase components.

We claim:

1. In the method of separating blood into its light, substantially liquid phase and its heavy, substantially cellular phase by providing a tubular blood collection container having disposed in its bottom an inert, flowable, gel-like barrier material; filling the container with blood; and centrifuging the blood filled container to effect separation of the phases and displacement of the barrier material to the interface between phases; the improvement which consists of providing means to cause said gel-like barrier to make a complete sealing contact with the entire inner surface of the tubular container at a predetermined level thereof, said means consisting of a constriction in the bore thereof, positioned in the zone where the barrier material is calculated to come to rest during centrifugation, said constriction being integrally formed and fixed in the wall of the said container; whereby during centrifugation, the barrier material displaced makes sealing contact with said constriction and closes the bore in said zone, permanently isolating the liquid phase from the cellular phase without destruction of the tubular container.

2. The method of claim 1 wherein the barrier material is disposed with a slanted top surface and the constriction is formed by an inward bulge of the container wall opposite the face of the slant.

3. The method of claim 1 wherein said constriction is an annular constriction.

* * * * *